United States Patent [19]

Perry

[11] Patent Number: Plant 5,827

[45] Date of Patent: Dec. 16, 1986

[54] ROSE PLANT

[75] Inventor: Anthony Perry, Hemet, Calif.

[73] Assignee: Co-Operative Rose Growers, Inc., Tyler, Tex.

[21] Appl. No.: 680,291

[22] Filed: Dec. 10, 1984

[51] Int. Cl.[4] ..... A01H 5/00

[52] U.S. Cl. ..... Plt./11

[58] Field of Search ..... Plt./11

*Primary Examiner*—Robert E. Bagwill

*Attorney, Agent, or Firm*—Vincent G. Gioia

[57] ABSTRACT

A new multi-colored hybrid tea rose variety of greyed purple and apricot orange coloring.

1 Drawing Figure

The present invention relates to a new and distinct variety of rose plant of the hybrid tea rose class, which was originated by my crossing as seed parent an unnamed, unpatented seedling of my creation and the rose known as "Sutters Gold" (U.S. Plant Pat. No. 885) as pollen parent. The denomination of this new variety is "Burway".

Among the novel characteristics possessed by this new variety which distinguish it from its parents and all other varieties of which I am aware are its flowers of unusual multi-coloring varying from greyed purple outer petal segments to apricot orange flower centers. The greyed purple coloring may vary from ¼ of outer petal to merely at outer petal edge. In the latter instance petal top surface appears pale pink with inner petals appearing apricot orange. Asexual reproduction by budding of the new variety as performed in Riverside County, Calif., shows that the foregoing and other distinguishing charateristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "184D" is plate 184D of The Royal Horticultural Society Colour Chart.

Parentage: Seedling.

*Seed parent.*—Unnamed seedling.

*Pollen parent.*—"Sutters Gold".

Class: Hybrid Tea.

The following observations are made of specimens grown outdoors in Riverside County, Calif., during the months of July and August.

FLOWER

Blooming habit: Recurrent.

A. Bud:

(1) *Size.*—Medium.

(2) *Form.*—Pointed.

(3) *Color.*—After sepals divide, buds are near 184D, but after sepals fall, complex coloring involving mixture of several hues including 185D suffused with 26D particularly toward point of petal attachment; veining is evident.

(4) *Sepals.*—Longer than bud, few appendages.

(5) *Peduncle.*—Length — long, heavy. Aspect — upright. Strength — erect, strong. Color — near 182A.

B. Bloom:

(1) *Size.*—Average size when fully expanded — about 4 to 4½ inches.

(2) *Borne.*—Singly, one to a stem; sometimes small clusters.

(3) *Form.*—High centered becoming flat upon opening, outer petals reflex sharply, imbricate at maturity.

(4) *Petalage.*—Number of petals under normal conditions — about 25 to 30.

(5) *Color.*—Complex colored bud opens into multicolored flower with greyed-purple coloring (near 184D to 185D) on outer ¼ of outer petal top surfaces. Color change on outermost petal into near 65D is more gradual than inner petal where color changes more abruptly. On top surfaces of inner petals there may be only a touch of greyed purple coloring at petal edge with petal coloring tending to lighten to either pale pink or pale orange, the latter color deepening in tonality at flower centers, approaching 171D to 26C/D. Veining is pronounced throughout.

C. Petals:

(1) *Texture.*—Medium to heavy.

(2) *Appearance.*—Inside satiny with veining, outside smooth.

(3) *Form.*—Acuminate, rounded petals often have pointed apices.

(4) *Arrangement.*—Imbricated.

(5) *Petaloids in center.*—Few.

(6) *Persistence.*—Average.

(7) *Fragrance.*—Some.

(8) *Lasting quality.*—Average.

REPRODUCTIVE ORGANS

A. Stamens, filaments and anthers:

*Arrangement and color.*—Abundant, regularly arranged around styles; orange to orange red.

B. Pollen: Color — Yellow.

C. Styles: Abundant, medium length.

D. Stigmas: Color — cream colored.

E. Hips: Globular, medium, orange-yellow, seeds do not protrude.

PLANT

A. Form: Tall, upright.

B. Growth: Vigorous, good branching.
*Height attained.*—5 to 6 feet.

C. Foliage: Compound 5 to 7 leaflets.
(1) *Size.*—Medium.
(2) *Quantity.*—Abundant.
(3) *Color.*—New foliage: Upper side — purplish green. Under side — purplish green. Old Foliage: Upper side — near 147A. Under side — near 147B.
(4) *Shape.*—Oval.
(5) *Texture.*—Upper side is leathery and under side is satiny.
(6) *Edge.*—Serrate.
(7) *Serration.*—Normal.
(8) *Leaf stem.*—Color — light green.
(9) *Stipules.*—Medium length.
(10) *Resistance to disease.*—Blackspot — good. Mildew — good. Rust — good.

D. Wood:

(1) *New wood.*—Color — light green. Bark — smooth.
(2) *Old wood.*—Color — darker green. Bark — smooth.

E. Thorns:
(1) *Thorns:* Quantity (main stalk) — ordinary. On laterals from stalk — average. Form — thin, slight recurve. Length — medium. Color — tan to greenish brown. Position — irregular.
(2) *Prickles.*—Ordinary on main stem and laterals.

F. Winter Hardiness: Needs winter protection in severe climate.

I claim:

1. A new and distinct variety of rose plant of the hybrid tea rose class, substantially as shown and described, characterized particularly by multi-colored blooms which in open stage may have greyed purple outer petal segments and apricot orange flower centers varying to greyed purple petal edges, pale pink petals and apricot orange flower centers.

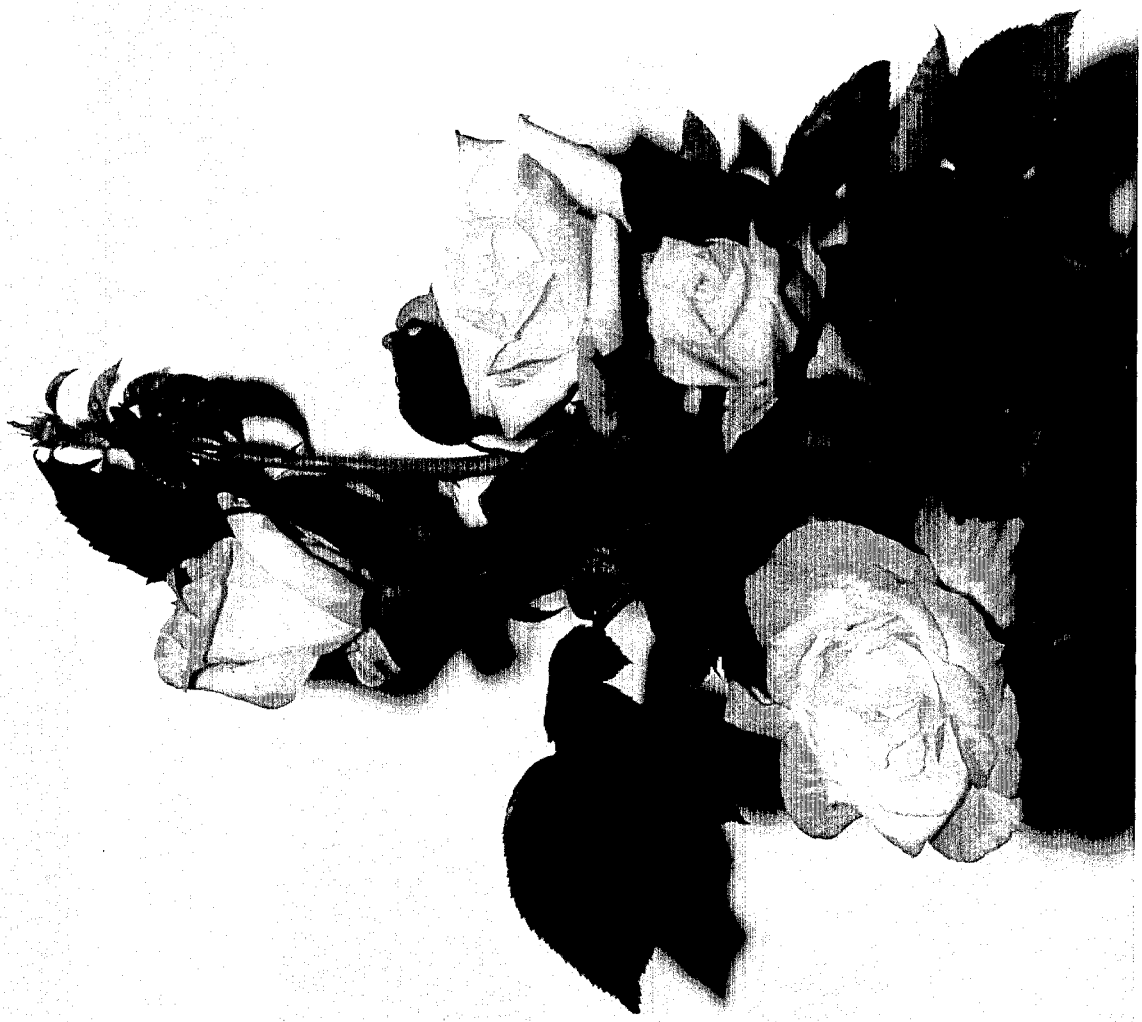

* * * * *